United States Patent
Shekarriz et al.

(10) Patent No.: US 7,560,013 B2
(45) Date of Patent: Jul. 14, 2009

(54) TREE FRUIT POSTHARVEST CHEMICAL SENSOR

(75) Inventors: Allroza Shekarriz, Lake Oswego, OR (US); W. Lloyd Allen, Vancouver, WA (US); Daniel James Faulkner, Portland, OR (US); Christopher M. Ward, Portland, OR (US); Debra M. Gilbuena, Hillsboro, OR (US)

(73) Assignee: Fluid Analytics, Inc., Portland, OR (US)

( * ) Notice: Subject to any disclaimer, the term of this patent is extended or adjusted under 35 U.S.C. 154(b) by 118 days.

(21) Appl. No.: 11/699,911

(22) Filed: Jan. 30, 2007

(65) Prior Publication Data

US 2007/0295203 A1 Dec. 27, 2007

Related U.S. Application Data

(60) Provisional application No. 60/815,892, filed on Jun. 22, 2006.

(51) Int. Cl.
*G01N 27/403* (2006.01)
(52) U.S. Cl. .................. 204/431; 204/409; 205/787
(58) Field of Classification Search .......... 204/400, 204/409, 431; 205/787
See application file for complete search history.

(56) References Cited

U.S. PATENT DOCUMENTS

RE31,915 E * 6/1985 Oswin et al. ............... 204/412
4,591,414 A * 5/1986 Zaromb et al. ............. 205/787
6,105,416 A   8/2000 Nelson et al.

FOREIGN PATENT DOCUMENTS

JP    8-298926 A   * 11/1996

OTHER PUBLICATIONS

Jordan et al, Analytical Chemistry, 69, pp. 558-562, 1997.*
Jordan et al, Analyst, 1997, 122, pp. 811-814.*
Bar-Cohen et al., Electro-Active Polymer (EAP) actuators for planetary applications, Proceedings of SPIE Annual International Symposium on smart structures and materials, Mar. 1999, paper No. 3669-05.

* cited by examiner

*Primary Examiner*—Kaj K Olsen
(74) *Attorney, Agent, or Firm*—Gary C Cohn, PLLC

(57) ABSTRACT

An electrochemical sensor for organic molecules such as ethylene includes an electrochemical cell, gas sample inlet means and means for detecting current produced by the oxidation of the organic molecule at the anode of the cell. The sensor is capable of sensing multiple organic molecules in some embodiments. A voltage is applied to the anode of the cell to provide energy to drive the oxidation reaction and produce a corresponding current. The sensor of the invention can be made as a small, hand-held unit that is capable of real-time detection of various organic species.

3 Claims, 6 Drawing Sheets

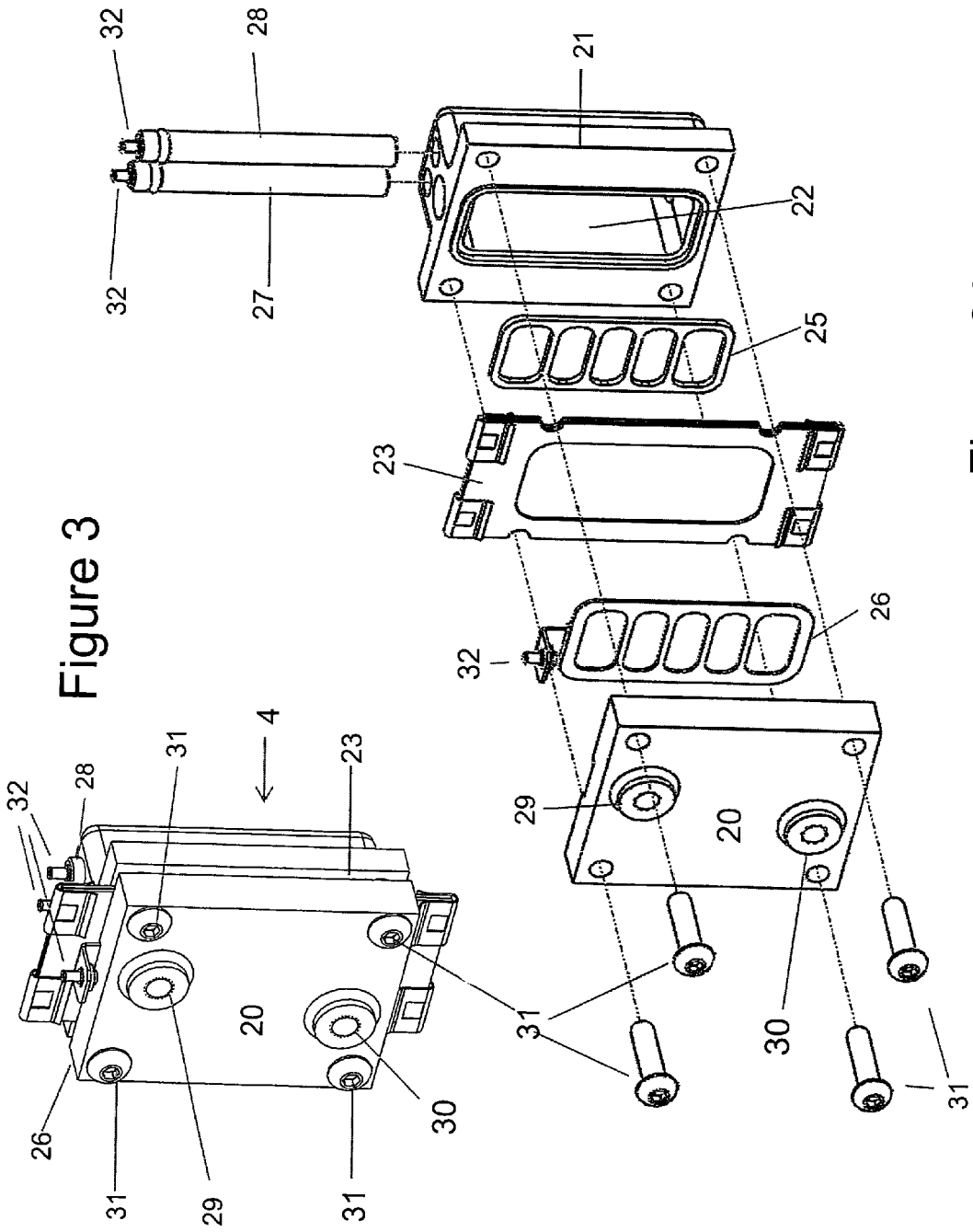

TREE FRUIT POSTHARVEST CHEMICAL SENSOR

CROSS-REFERENCE TO RELATED APPLICATION

This application claims benefit of U.S. Provisional Application No. 60/815,892, filed 22 Jun. 2006.

BACKGROUND OF THE INVENTION

There is a continuing trend throughout the world toward consumption of more fresh and minimally processed food. High quality fresh fruits and vegetables are now available year round, thanks to improved packaging, storage technologies and rapid global transportation. The abundance of year-round fresh produce is dependent on a vast infrastructure including specialized refrigerated storage facilities.

Maintaining the freshness of fruit, vegetables, and other horticultural products such as fresh cut flowers is very important to the postharvest industry and producers during various stages of transportation and storage. One of the ways to control the freshness of produce is by regulating its exposure to ethylene. Plants are very sensitive to ethylene concentration mainly because ethylene is one of their growth hormones. When produce has a limited exposure to ethylene, its natural aging process will be slowed. Yet, if ethylene concentrations reach a high enough level, produce will not only age faster, but begin to decay.

Ethylene production rate and the amount of ethylene present in the environment surrounding a single apple or pear (or in general for climacteric fruit) have been shown to affect the quality of these fruit during various stages of ripening. This is especially true post-harvest, where the rate of ripening, scalding, browning, and other issues could prevent high quality fruit from reaching the market.

A number of researchers are currently using various methods supported by a Gas Chromatography system (GC) to research the different aspects of interaction of ethylene and fruit quality at various pre- and post-harvest stages. While significant amount of data has been accumulated and a large of body of literature exists on varieties such as Bartlett pears and golden delicious apples, little information is available for some of the newer varieties such as Comice pears (and honey crisp apples). Research performed on Bartlett pears suggested that very low ethylene concentrations of less than 1 ppm have to be maintained to control fruit quality, which is difficult due to high ethylene production of fruit even at −1° C. storage temperatures. For such tight control, continuous monitoring of the ethylene levels in the storage facilities is required. There is currently no cost-effective real-time ethylene sensor in the market that can produce reliable measurements of ethylene at 0.1 ppm, the level required for control in storage areas.

In general, the ethylene-related problems result when coexistence of high ethylene-producing fresh fruit and vegetables (FF&V) are placed in the same storage area with highly ethylene sensitive FF&V (or cut flowers). For example, avocados and apples are known to produce extremely high ethylene levels even at less than 4° C. On the other hand, kiwifruit is not a high ethylene producer, but is extremely sensitive to the presence of ethylene and should not be stored where it might be exposed to significant amounts of ethylene. As little as 5 to 10 ppb (0.005 to 0.010 ppm) ethylene in a storage atmosphere can accelerate softening without impacting other ripening processes. This results in unripe fruit that are excessively soft. Carrots produce very small amounts of ethylene at (<0.1 µL $kg^{-1}$ $h^{-1}$ at 20° C.). However, exposure to exogenous ethylene (~0.2-ppm) will induce development of isocoumarin and bitter flavor in carrots. While separating the various fruit and vegetables in cold storage may seem like a logical approach to cold storage, it is impractical to have a separate cold storage area for every cultivar of FF&V.

Ethylene monitoring is currently not a widely adopted process in many packing houses and cold storage facilities. Some ethylene sensors are limited in detection accuracy and those with significant accuracy are too large (suitcase size) and too expensive (several thousand dollars) for packing houses to afford and use. Localization of more rapidly ripening fruit that is the source of ethylene is challenged by the high cost and inconvenience in detection. Such localization could provide strategies to minimize ethylene production and to control spoilage and rapid ripening process.

These problems can be addressed if a cost effective, preferably compact ethylene detection method is made available to warehouses and/or to growers for monitoring ethylene in storage environments and in orchards to monitor the ripening process prior to harvesting.

The most basic existing technology for ethylene measurement is to take an air sample, then later test it at one's convenience for ethylene concentrations under laboratory conditions. For example, an air sample may be gathered in a sample bag and sent to the lab for testing. This technique gives one measurement of ethylene concentration whose accuracy is only limited in accuracy by the way that the sample is taken and tested. The main draw back to this technique is that the ethylene concentration is not known in real time—there is a delay associated with the sampling and testing. Due to the cumbersome nature of the process, this technique is not practical for continuous ethylene monitoring.

Another current technology for ethylene measurement is to use a sampling pump to draw air through a detector tube. A detector tube is a small tube that when air is pumped over it, the concentration of a particular gas is indicated. This is normally done by means of a color change shown on graduations along the side of the detection tube. The resolution of this technique is only as good as one can read the color change. This technique is also limited by the use of one time, disposable tubes. The detection tube can be exposed to air either by means of a hand pump (such as Sensidyne's AP-1S) or by a mechanical pump that draws air more slowly across the detection tube, to provide a reading averaged over a longer period (such as Sensidyne's GilAir5). Again, this technology is not suitable for continuously monitoring ethylene concentrations in environments such as de-greening rooms.

Personal air samplers are a very commonly used technology for measuring ethylene concentrations in de-greening rooms. These are often hand held or belt clip air samplers that give real time information on various gas concentrations. The detection is accomplished by using a metal oxide such as tin oxide to detect changes in surface resistance as a gas is adsorbed onto the surface. Although this technique can provide real time information, it has a limited resolution of 1 ppm or higher.

Another ethylene sensing technology is based on the chemiluminescence reaction of ethylene and ozone. Chemiluminescence of the ozone-ethylene reaction has been extensively studied and is well-documented in the literature. Most of these studies were triggered by the desire to accurately measure the ozone level in the atmosphere or for the process industry where monitoring and control of ozone is important. Surprisingly, the reverse has been less of interest to most of the researchers with the exception of one study and group at Geo-Centers, Inc. In summary, the reaction of ethylene with ozone produces a number of intermediate products, including the light emitting species $OH^+$ and $HCHO^*$ at excited state. When these intermediate species decay, they release energy in the form of electromagnetic (EM) radiation or photons, with energy of hv. Detailed spectra of the emissive power from these decaying molecules reveal EM radiation energy at several different wavelengths, ranging between UV to IR, including visible radiation.

U.S. Pat. No. 6,105,416 describes an ethylene detector based on chemiluminescence. This detector requires that the ethylene sample and ozone be pumped concurrently into a pressurized test chamber that also has ozone concurrently being pumped in under pressure. Pressurized ozone is used because a higher reagent concentration of ozone increases the likelihood that the ozone will react with ethylene, thus increasing the system's efficiency and signal to noise ratio. The ozone used is created internally by means of a separate ozone generator that is fed either compressed air, or compressed oxygen. These ethylene detection systems, operating by means of discrete test chambers, ozone generators, and various valving for the pressurized gasses tend to be large, cumbersome and very expensive. Furthermore, generation of ozone in a high-pressure oxygen or air environment poses the risk of explosion and can be deemed hazardous. Because of cost limitations, only one system within the entire de-greening building (with individual sampling lines routed to each degreening room) can be used, making it unsuitable and expensive for localization of the ripening process.

What is needed is an inexpensive, light-weight, portable sensor that is capable of accurately detecting the presence of a target organic molecule in a sample gas such as air at concentrations of less than 1 ppm.

SUMMARY OF THE INVENTION

This invention is in certain aspects a sensor comprising a) an electrolytic cell having an anode that adsorbs a gas-borne target organic molecule, b) means for measuring current created by a reaction of the gas-borne target organic molecule at the anode, c) and intake means for supplying a sample gas to the anode. The sensor preferably comprises means for supplying a predetermined voltage to the anode. The sensor preferably includes gas movement means for transporting the sample gas through the intake means to the surface of the anode. The sensor also preferably comprises a human-readable display which indicates the presence or absence of the target organic molecule in measurable quantities in the sample gas and optionally the concentration of such target organic molecule in the sample gas. The sensor also preferably includes an electrical power source and/or means for connection to an electrical power source. The sensor of the invention is preferably miniaturized, having a longest dimension of 12" (30 cm) or less, preferably 8" (20 cm) or less, a volume of 128 in$^3$ (~2100 cm$^3$) or less, preferably 64 in$^3$ (~1050 cm$^3$) or less, especially 48 in$^3$ (~785 cm$^3$) or less, and a weight of 2 pounds (0.9 kg) or less, preferably 1 pound (0.45 kg) or less.

The electrochemical sensor of the invention is capable of oxidizing ethylene and other target organic molecules to create an electrical current, providing a direct measure of the presence of ethylene in a gas stream. The sensor can in some embodiments detect the presence of ethylene at concentrations of less than 1 ppm, in some embodiments less than 100 ppb and in some preferred embodiments at concentrations of less than 10 ppb in the gas stream.

The electrochemical sensor of the invention is capable of discriminating between different target organic molecules by controlling the electrolyte solution chemistry, choice of electrode material, and applied potential. By using multiple sensing elements in parallel or in series along the sampling flow direction, different target organic molecules can be detected simultaneously and distinguished from each other both qualitatively and quantitatively.

The invention is also a process for determining the presence and/or concentration of a target organic molecule in a gas stream, comprising bringing the gas stream in contact with an anode of an electrolytic cell under conditions such that the target organic molecule is oxidized at the surface of the anode to create an electrical current, and detecting and/or measuring the electrical current created by the oxidation of the target organic molecule.

In another aspect, this invention is a system for removing one or more target organic molecules from a gas, the system comprising 1) an electrochemical sensor that includes at least a) an electrolytic cell having an anode that adsorbs a gas-borne target organic molecule, such that the target organic molecule undergoes a reaction at the anode and produces a current and b) intake means for supplying a sample gas to the anode; and c) means for generating a control signal in response to the current produced by said reaction of the target organic molecule at the anode, and 2) a scrubbing device for removing the target molecule from a gas, wherein the scrubbing device is operable in response to the control signal produced by the electrochemical sensor.

In yet another aspect, this invention is a process for removing a target organic molecule from a gas, comprising 1) bringing the gas or a sample thereof into contact with an anode of an electrolytic cell under conditions such that the target organic molecule is oxidized at the surface of the anode to create an electrical current indicative of the presence of the target organic molecule in the gas or sample thereof, and 2) when the target organic molecule is present in the gas or sample at a predetermined level, as indicated by the creation of the electrical current, scrubbing the gas or portion thereof to remove the target organic molecule.

In another aspect, the invention is a process for removing a target organic molecule from a gas, comprising 1) bringing the gas or a sample thereof into contact with an anode of an electrolytic cell under conditions such that the target organic molecule is oxidized at the surface of the anode to create an electrical current indicative of the presence of the target organic molecule in the gas or sample thereof, 2) when the target organic molecule is present in the gas or sample at a predetermined level, as indicated by the creation of the electrical current, contacting the gas or a portion thereof with ozone under conditions such that the ozone reacts with the target organic molecule to convert the target organic molecule to another species.

In another aspect, the invention is a process for detecting and removing a target organic molecule from a gas, comprising 1) periodically or continuously bringing the gas or a sample thereof into contact with an anode of an electrolytic cell under conditions such that, when present, the target organic molecule is oxidized at the surface of the anode to create an electrical current indicative of the presence of the target organic molecule in the gas or sample thereof, 2) when the target organic molecule is present in the gas or sample at least at a predetermined level, as indicated by the creation of the electrical current, contacting the gas or a portion thereof with ozone under conditions such that the ozone reacts with the target organic molecule to convert the target organic molecule to another species, and 3) when the target organic molecule is not present in the gas or sample at least at a predetermined level, as indicated by the creation of the electrical current or lack thereof, discontinuing contacting the gas or a portion thereof with ozone.

In another aspect, the invention is a process for removing a target organic molecule from a gas, comprising 1) bringing the gas or a sample thereof into contact with an anode of an electrolytic cell under conditions such that the target organic molecule is oxidized at the surface of the anode to create an electrical current indicative of the presence and concentration of the target organic molecule in the gas or sample thereof, 2) treating the gas or portion thereof with ozone in response to the electrical signal such that the ozone reacts with the target organic molecule to convert the target organic molecule to another species, by 2-a) estimating the number of moles of the target organic molecule in the gas or portion thereof to be treated 2-b) generating ozone in response to the electrical current and 3) contacting the gas or a portion thereof with the ozone under conditions such that the ozone reacts with the target organic molecule to convert the target organic molecule to another species, wherein the amount of ozone that is generated is no more than about 1.5 moles of ozone per mole of target organic molecule in the gas or portion thereof contacted with the ozone.

BRIEF DESCRIPTION OF THE DRAWINGS

FIG. 3 is an isometric view of an electrolytic cell for use in the invention.

FIG. 3A is an exploded view of the electrolytic cell of FIG. 3.

DETAILED DESCRIPTION OF THE INVENTION

Figure 1:
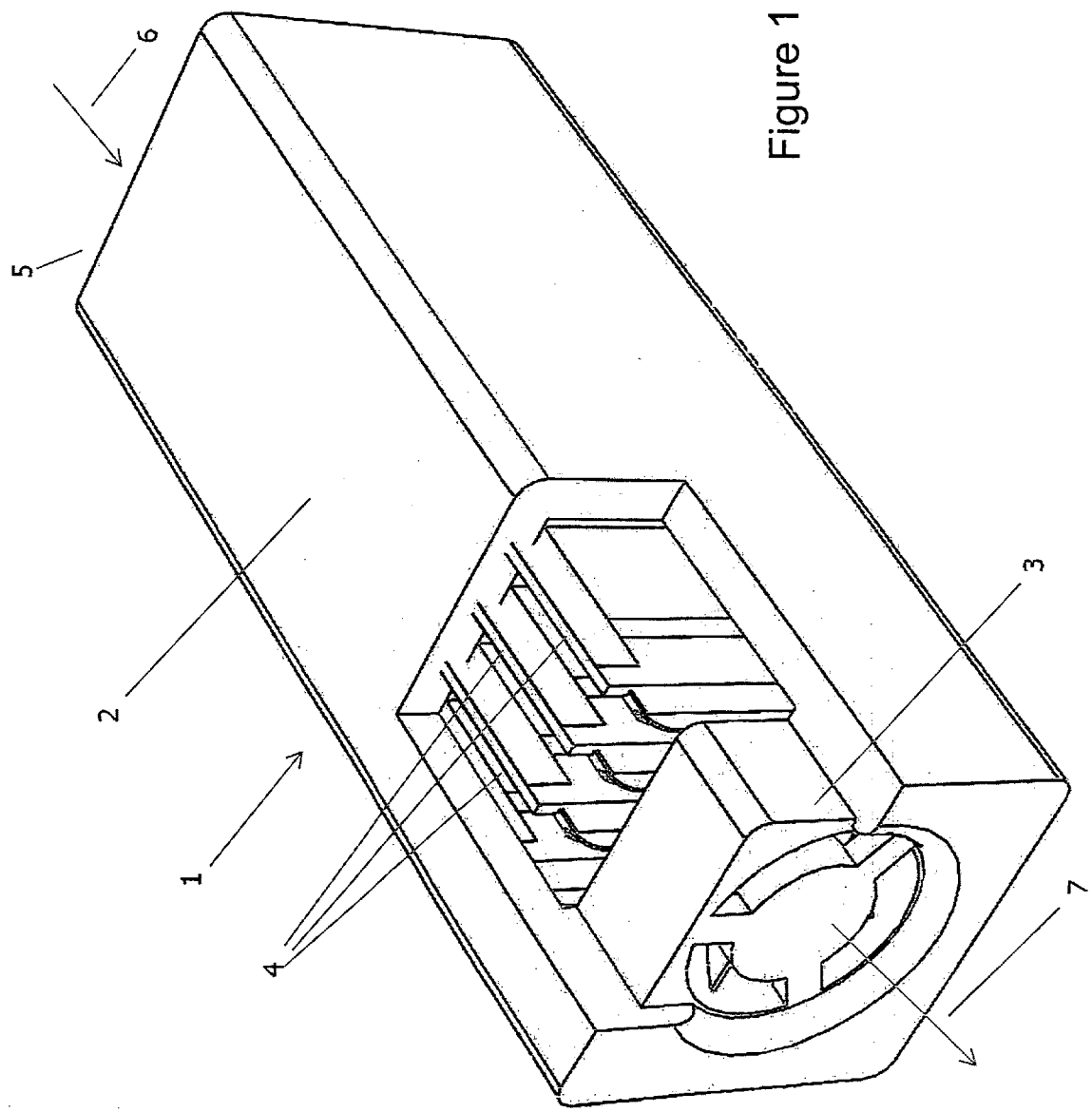
FIG. 1 is an isometric view of an embodiment of the invention.

Turning to FIG. 1, sensor 1 includes housing 2, which is shown partially in section to reveal internal components. Housing 2 contains a miniature blower 3 which moves sample gas through the sensor. In this embodiment, multiple electrolytic cells 4 are aligned within housing 2. Electrolytic cells 4 have anodes that are exposed to the passing sample gas. Spaces between the aligned electrolytic cells 4 form channels through which the sample gas is brought into the sensor and into contact with the anode of the electrolytic cells. Circuitry (not shown in FIG. 1) provides a predetermined potential to the anode surface so a target organic molecule becomes oxidized at the anode surface. The circuitry also includes means for measuring current produced as a result of the oxidation reaction. Housing 2 has openings at end 5 which serve as intakes for supplying the sample gas to the anode surfaces. In the embodiment shown, blower 3 moves the gas through sensor 1 in the direction indicated by arrow 7, but in principal the gas can be moved in either direction through sensor 1. This arrangement provides an approach for obtaining very high sensitivity for detection of a single target organic molecule or for simultaneous detection of multiple target organic molecules.

Figure 2:
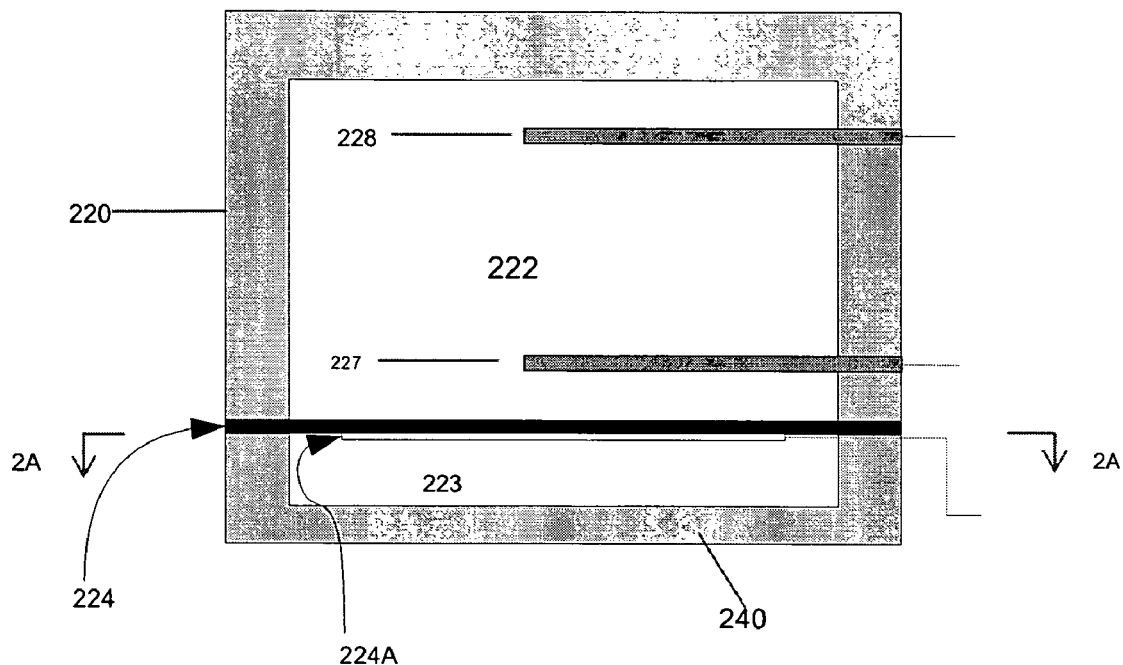
FIG. 2 is a top sectional view of an electrolytic cell for use in the invention.
Figure 2A:
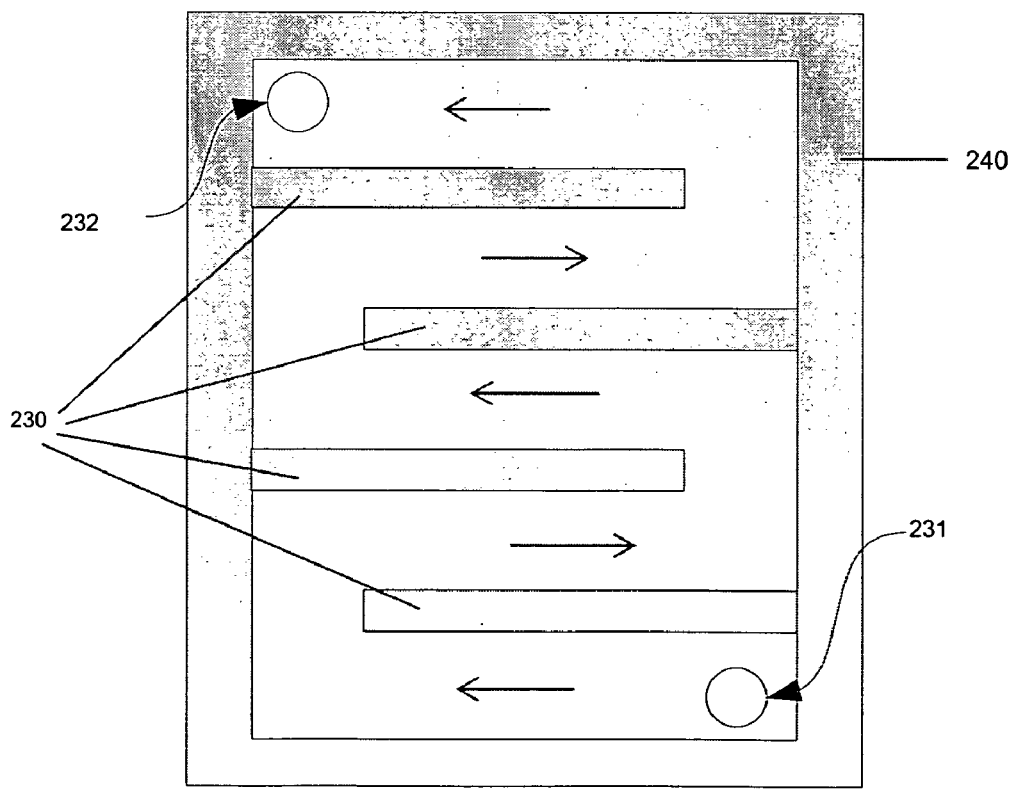
FIG. 2A is a sectional view of a baffled air chamber cap of an electrolytic cell for use in the invention.

FIG. 2 is a diagram of a simple electrolytic cell for use in the invention. Housing 220 and anode 224 together define cavity 222, which holds an electrolyte. Counter electrode 227 is in electrical contact with the electrolyte inside cavity 22. Optional reference electrode 228 also is in electric contact with the electrolyte inside cavity 222. Cap 240 and anode 224 define sample chamber 223 where sample gas is brought into contact with anode 224. Anode 224 is impermeable to the electrolyte so the electrolyte does not leak into sample chamber 223. Anode 224 includes a surface metal layer 224A which is exposed to the sample chamber 223 where it can be contacted with a sample gas. As shown in FIG. 2A, cap 240 includes an inlet for introducing the gas sample into zone 223 and outlet 232 for removing the gas sample. In FIG. 2A, inlet 231 is a simple opening and the outlet 232 is a simple outlet port. These may be gated or valved in various manners if desired. Inlet 231 is in fluid communication with a source of the sample gas. Preferably, the sensor will include or be connected to some means, such as a fan, blower, or pump (not shown) which can effect mass transfer of the sample gas through sample chamber 223. As shown, cap 240 includes baffles 230 which direct the flow of sample gas over a large portion of the surface area of anode 240. The direction of bulk blow is indicated in FIG. 2A by the arrows. Baffles and similar can also serve to create turbulent flow of the sample gas.

FIGS. 3 and 3A illustrate a specific design for the electrolytic cell. In FIGS. 3 and 3A, front housing 20 includes gas inlet 29 and gas outlet 30. Rear housing 21 includes cavity 22 which holds the electrolyte of the cell. Working electrode 27 and reference electrode 28 are inserted into cavity 22 of rear housing 21, where they are in contact with the electrolyte contained in cavity 22. Frame 23 is sandwiched between front housing 20 and rear housing 21. Frame 23 holds anode 24. Mechanical support 25 is interposed between anode 24 and cavity 22 of rear housing 21. Mechanical support 25 includes openings which permit anode 24 to be exposed to the electrolyte which is contained in cavity 22 of rear housing 21. Working electrode 26 is in electrical contact with anode 24, and serves as an electrical conduit between anode 24 and the power supply. As shown in this embodiment, working electrode 26 has openings which permit sample gas entering front housing 20 to make contact with anode 24. Electrodes 26, 27 and 28 each have connections 32 for connection to circuitry and an electrical power source which will be described more fully below. Screws or rivets 31 hold the assembly together.

Figure 4A:
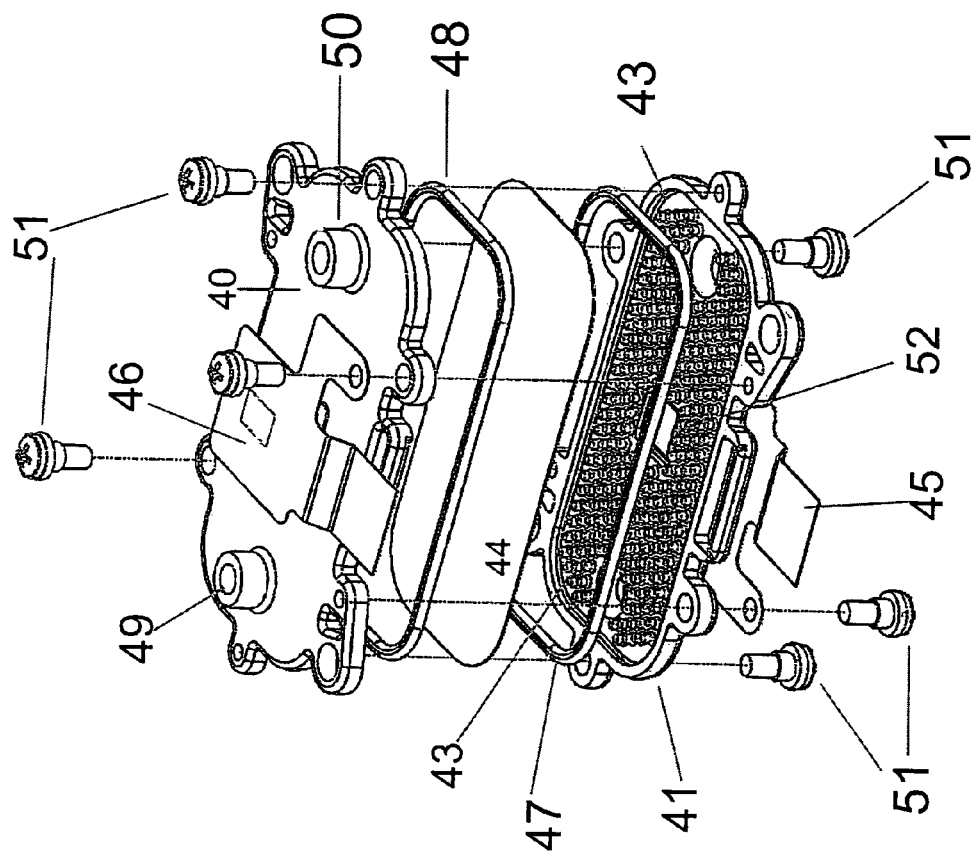
FIG. 4A is an exploded view of the electrolytic cell of FIG. 4.
Figure 4:
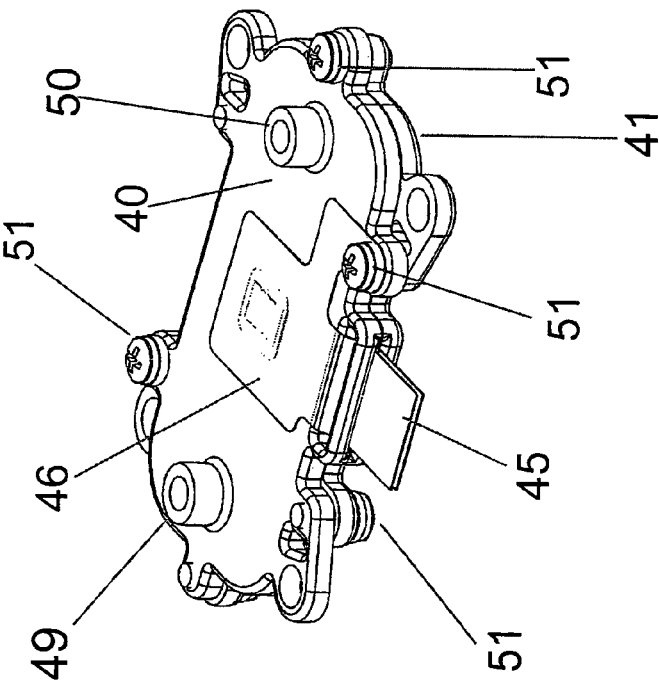
FIG. 4 is an isometric view of another electrolytic cell for use in the invention.

FIG. 4 is an isometric view of another embodiment of the electrolytic cell 37, and FIG. 4A is an exploded view thereof. Top housing 40 includes gas inlet 49 and gas outlet 50. Bottom housing 41 defines cavity 42 which holds the electrolyte of the cell. Bottom housing 41 will typically include inlet and outlet ports (not shown) for filling, emptying and recirculation of the electrolyte. Optional support pegs 43 provide mechanical support and higher current collection capability to anode 44. Anode 44 is positioned between top housing 40 and bottom housing 41. Anode 44 is exposed on one side to a recirculating or stagnant electrolyte which is contained in cavity 42 of rear housing 41, and on the other side to the flowing sample gas that enters top housing 40 through gas inlet 49. Seals 47 and 48 protect against leakage of electrolyte and sample gas from electrolyte cell 4. Screws or rivets 51 hold the assembly together. In this embodiment, top housing 40 functions as a working electrode, and is in electrical contact with anode 44. Voltage is supplied to top housing 40 via flex circuit 46, which may also contain or be connected with temperature and/or humidity sensors. Similarly, bottom housing 41 functions as a working electrode in this embodiment, with voltage being supplied via flex circuit 45. Flex circuit 45 may also contain a reference electrode and may contain or be connected to temperature and/or humidity sensors. Flex circuits 45 and 46 are connected to additional circuitry and/or an electrical power source as described more fully below.

The anode of the electrolytic cell has a metal surface. The metal is one that (1) adsorbs the target molecule and (b) catalyzes the oxidation of the target organic molecule at the anode surface. Preferred metals are gold, silver, copper and platinum, with gold being of particular interest. The anode is also preferably permeable to water and hydrogen or other small ions, particularly cations, that are produced in the oxidation reaction. A preferred anode is a solid, semi-permeable membrane that is coated or plated with the anode metal. An example of a membrane material is an ionomer film such as a sulfonated fluoropolymer film. Such films are available commercially as Nafion® films. The anode may be roughened, deformed, or embossed to have microstructures such as micropins, riblets, grooves, of corrugations to provide a higher exposed surface area. The plated metal preferably has a somewhat roughened surface as typically appears when the deposited metal is in a microcrystalline state. The plated metal may have some discontinuities, in the form of pores, cracks or the like which allow small molecules or ions to pass through the plated metal during the oxidation reaction, as needed to complete the oxidation reaction.

A suitable method for plating a polymer electrolyte with gold or other metal is described, for example, in Jordan and Hauser, *Anal. Chem.* 69, 558-562, 1997, and Cook, *Journal of the Electrochemical Society*, 235, 187-189, 1990. In general, a film of polymer electrolyte is bathed in a solution of a soluble metal compound, typically a halide or a sulfide, to absorb the metal compound onto the electrolyte surface. The absorbed metal compound is reduced at the surface of the polymer electrolyte by contacting the polymer electrolyte with a reducing solution. In preferred cases in which the polymer electrolyte is semi-permeable, a film of the polymer can be used to divide a cell into two sections, one of which contains the metal compound solution and one of which contains the reducing agent solution. In this manner, the polymer electrolyte can be bathed in both solutions simultaneously, with the plating reaction occurring on or within the polymer electrolyte. Suitable metal compounds are halides of the metal to be plated, such as silver chloride, copper chloride, gold chloride, gold hydrogen chloride ($HAuCl_4$) and the like. Suitable reducing agents include borohydride salts such as sodium borohydride and sodium bisulfite. These solutions can be stabilized by adjusting their pH into the basic range such as by addition of caustic.

The anode may be supported if necessary to minimize or eliminate flexing during operation. Flexing or other movement of the anode may lead to inaccuracies or variations in the current produced during operation of the sensor.

In the electrolytic cell, the anode is placed into contact with an electrolyte, which may be liquid, solid or a gel. The electrolyte is capable of transporting ions from the anode (working electrode) to the cathode (counter electrode) of the cell and in that manner completes the chemical reaction. A suitable electrolyte is an aqueous solution that contains a mineral acid such as sulfuric or hydrochloric acid. The electrolyte may contain other acids or buffers, as well as preservatives, thickeners, gelling agents and other useful components. An electrolyte of particular interest is a solution of 0.01 to 5 M sulfuric acid or hydrochloric acid, although other mineral acids and even organic acids are suitable. The molarity is more preferably from about 0.05 to 1.0 M. The electrolyte may be sealed within a case, housing or other system which prevents leakage and isolates the electrolyte from the outside environment.

A stationary electrolyte (i.e., one that remains in the electrolytic cell) may be used. In such cases, it is preferred to provide the cell housing with a venting means, by which gasses can enter and exit the cell to balance pressures. The venting means should be substantially impermeable to the electrolyte so leakage does not occur. A suitable venting means is a small window of a gas-permeable membrane in the housing of the cell. Such a membrane can permit gas (typically air or inert gas not containing the target organic molecule(s)) to enter the cell to balance pressures, and to allow hydrogen or other gasses formed in the electrochemical reaction(s) to vent. A suitable gas-permeable membrane is a polytetrafluoroethylene polymer such as a Gore-Tex membrane, or similar type of membrane.

Alternatively, the electrolyte may be circulated through the cell, for example, by being pumped through the cell from a reservoir. In such cases, it is usually not necessary to provide separate venting.

The electrolyte preferably is maintained at constant pH, temperature, and quantity in the cell cavity during operation, in order to maintain a uniform response to the presence of the target organic molecule. The desired temperature range for the electrolyte is between 0° C. and 1001° C., although the more preferred range is between 10° C. and 40° C., and even more preferred range is between 15° C. and 30° C. There should be sufficient amount of electrolyte solution to fill the cell cavity such that it coats the entire exposed surface area of the polymer electrolyte. As shown in FIG. 4, the case or housing can also function as the anode, cathode and/or reference electrode, if the case is sufficiently electrically conductive.

The electrolytic cell also includes at least one counter electrode (cathode) which can be made of any conductive material, and may be made of the same metal as is used in the anode. The cathode is in electrical contact with the electrolyte but not in electrical contact with the anode, except through the electrolyte. The electrolytic cell also includes a reference electrode against which the potential of the anode is measured.

The electrolytic cell can be formed onto an electrochemical card having external electrical contacts which permit the card to be plugged into a housing in the manner shown in FIG. 1. Each card is packaged to contain an electrolyte in a sealed unit with the counter electrode fully sealed within it. The anode surfaces are exposed on one or preferably both sides of the card. In the embodiment shown in FIG. 1, housing 2 has corresponding electrical contacts which permit a voltage to be applied across each such electrical chemical card. The cards can be plugged into the housing, in the manner shown in FIG. 1, with separate or common electrical connections for the anodes and the counter electrodes, depending, for example, on the number of target organic molecules to be detected simultaneously. The number of target organic molecules that can be detected at one time is generally limited by the number of cards used in the cell assembly. Once plugged in the chassis, the spaces between the consecutive cards form microchannels for flow of the sample gas.

If multiple electrochemical cards are present in a single housing (as shown in FIG. 1, the individual cards may be identical to each other. In such a case, the sensor can be operated to detect a single, specific target organic molecule (by applying the same voltage to each cell), or to detect multiple target organic molecules (by applying different voltages to some of the cells). Alternatively, the individual electrochemical cards may contain different electrolytes or different anodes, which permit them to detect to different target organic molecules. This permits the sensor to simultaneously detect multiple target organic molecules, in some cases even when all the cards are operated at the same applied voltages.

As shown in FIG. 1, the sensor of the invention includes at least one intake means, through which the sample gas is introduced to the sensor and is brought into contact with the anode of the electrolytic cell. The intake means may be any type of conduit through which the sample gas can enter the sensor and reach the anode surface.

The sensor will also typically include outlet means through which sample gases can be discharged. Suitable outlet means are any type of channel through which the sample gas can be discharged from the sensor.

The intake or outlet means may further include some means such as a fan, blower, bellows or the like which creates a flow of the sample gas through the intake means to the electrode. A miniature fan is especially suitable. The means for moving the sample gas is preferably electrically operated, and especially preferably is operable using a small DC current as can be provided by a battery.

The design of the intake means is not particularly critical, provided that the sample gas makes good contact with the anode such that the target gas can be adsorbed and oxidized. The sample gas may be directed onto the anode at an acute angle (such as 45-90° to the anode surface). The acute angle of impact helps to ensure that all target molecules contact the anode surface where they can be adsorbed and oxidized. Such a configuration tends to cause large pressure drops within the device, and can require larger anode surface areas. An alternate way of getting good contact of the target molecules with the anode is to reduce its mass transfer timescale through the use of a turbulent flow of the sample gas or reduce channel size through which the gas is flowing, at least at the point at which the sample gas contacts the anode. Turbulent flow is characterized by a Reynolds number of at least 5, preferably at least 500. Under these turbulent flow conditions, the sensor of the invention often exhibits a very linear response with respect to target molecule concentration. It is especially preferred to achieve such flow conditions at flow rates of from 5 to 3000, especially 100 to 1000 standard cubic centimeters/minute (sccm), most preferably from 200 to 500 sccm.

Small mass transfer timescale is more easily achieved, at a given flow rate, through the use of smaller channels. Such microchannel geometry lends itself to parallelization, in which a number of channels can be stacked together for much higher system throughput and signal strength in a compact package. The design is simple and rather insensitive to the flow variations beyond a given threshold and by going to the microchannel scales one can reduce the flow requirements for further system compaction and reduce power requirements. If desired, the flow from the microchannels can be directed to multiple anodes (forming parts of multiple electrolytic cells of the type described before). Stacking a number of these microchannels in this way increases the current that is produced from the oxidation of the target organic molecule, which makes signal detection and measurement easier and more precise. Mass transfer rates increase inversely with the hydraulic diameter of the microchannel, and multiple microchannels operating in parallel provides a very high surface area for reaction, yielding significantly higher signal strength.

Smaller mass transfer timescales can be further achieved by placing surface features, such as ribs or other protrusions, on the surfaces of the intake means. The combination of the use of smaller channels with surface features such as these leads to a much higher signal-to-noise-ratio in a compact geometry. A tortuous flow path can cause turbulent flow of the gas as it approaches the anode, again leading to smaller mass transfer timescales.

The sensor also includes means for applying a predetermined electrical voltage to the anode, and means for measuring electrical conditions (typically current) produced when the target molecule is oxidized at the anode. A simple galvanometer or potentiostat is suitable for accomplishing both of these things. Preferred devices are capable of imposing a potential of from 0.1 to 2.5, especially from 0.5 to 1.5 volts to the anode, relative to a standard hydrogen electrode (SHE), and of measuring currents in the range of from 1 nA to 100 mA, especially from 0.1 µA to 1 mA.

The circuitry may be, for example, an analog circuit which uses a pair of op amps, one as a biased emitter follower to provide the desired potential to the cell, and the other as a signal amplifier to measure the current produced by the cell. The circuitry may be digitally controlled, which facilitates real-time control of the applied voltage, baseline offsets and signal amplifier gain.

A number of commercially available galvanometers and potentiostats are useful. An example of a suitable potentiostat is a Model 273-A potentiostat/galvanostat from Princeton Applied Research, Oak Ridge, Tenn., operated with CorrWare software (from Scribner Associates, Southern Pines, N.C.). Another suitable potentiometer is a Custom Sensor Solutions model 1401 potentiostat.

The sensor preferably includes at least one human-readable display which, in response to the electrical conditions created by the oxidation of a target organic molecule at the anode, indicates the presence or absence of the target organic molecule in measurable quantities in the sample gas and/or the concentration of such target organic molecule in the sample gas. The display can be a visual type, a sonic type or some other suitable type. Combinations of various types can be used. A simple type of display is a light, such as an LED, which can be turned off or on (or display different colors) to indicate the presence or absence of the target molecule. For example, such a light can be set to be "off" until a target molecule is detected, in which case it becomes activated. A more complex display can be an LCD display, which can be designed to indicate the qualitative presence or absence of the target molecule, or which can provide quantitative information as to the concentration of target molecule in the sample gas stream.

The sensor also preferably includes an electrical power source and/or means for connection to an electrical power source. A suitable electrical power source is a battery, but an AC source in combination with a transformer (to produce DC power) can also be used.

During operation, a flowing stream of the sample gas is passed over the anode. When an electrical potential is applied across the anode and cathode, target organic molecules that are adsorbed on the surface become oxidized. The sensor is suitable for use with any organic molecule that is capable of being oxidized at a potential lower than that at which the metal on the anode becomes oxidized. A higher potential than the metal oxidation threshold can be used for accelerated or enhanced electrocatalytic oxidation and/or destruction of the target organic molecules in cases where sensing the concentration of the target organic molecule is not critical. One may use two cells in parallel or series operating at two different potentials, in which one cell is tuned for detection of the target organic molecule and the second cell is tuned for accelerated destruction of the target organic molecule. The first cell can be operated in response to a current produced by the first cell, indicating the presence of the target organic molecule in the gas sample. In such a case, the first cell functions as a controller for the operation of the second cell, which operates in response to the detection of the target organic molecule (at or above some threshold level) by the first cell.

The electrochemical sensor of the invention is especially sensitive to organic molecules that have a carbon-carbon double bond, but it can also respond to compounds containing a carbon-oxygen double bond, a sulfur-oxygen double bond, a carbon-carbon triple bond, and molecules containing $\pi^*$ bond(s) where the $\pi^*$ bond interactions with the anode metal results in strong complexation and adsorption onto the surface of the anode.

Small organic molecules such as $C_2$-$C_8$ alkenes, halogenated alkanes and halogenated alkenes and the like are of particular interest as the target organic molecule. Alkenes, particularly ethylene, are of major interest. The target organic molecule to be detected is matched with the metal on the anode in a way such that the target organic molecule is oxidized below the metal oxidation threshold. Ethylene, for example, has an oxidation threshold lower than that of gold, which makes gold a suitable metal for the anode when sensing ethylene. When oxidized, ethylene molecules are converted to acetaldehyde at the triple-phase boundary where the anode, sample gas and electrolyte molecules and ions come together, according to the following idealized equation:

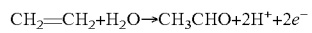

$$CH_2=CH_2+H_2O \rightarrow CH_3CHO+2H^++2e^-$$

The electrons that are produced create a current which can be measured to indicate the presence and/or concentration of ethylene in the sample gas. The protons migrate through the anode into the electrolyte and across to the counter cathode to complete the cell circuit.

The oxidation reaction requires the presence of an oxidant, which can be oxygen present in the gas sample but more typically is water due to the requirement for ion migration path to the electrolyte. Water molecules can be provided in the gas samples (such as ambient humidity in an air sample), or can be provided by water molecules from the electrolyte solution, which can permeate the anode and thus become available for reaction at the anode surface. It is possible to add an oxidant to the sample gas for enhanced reaction at the anode surface.

The amount of current produced (for a given concentration of the target organic molecule in the sample gas) is controlled largely by the rate of diffusion of the target molecule from the freestream to the anode and the rate of diffusion, adsorption, and reaction of target organic molecule inside the anode pore space. The rate of conductance of ions in the electrolyte and the rate of migration of ions and molecules to the anode are believed to have a smaller effect on the amount of current that is produced.

The oxidation of the target organic molecule takes place at or above a specific potential that is maintained while measuring the currents. The level of current generated for this given potential is proportional to the partial pressure of the target organic molecule in the gas stream, which is typically a function of its concentration. The sensor often is able to quantitatively detect levels of target organic molecule (particularly ethylene) down to 100 ppb with high confidence level, further down to 10 ppb with slightly lower confidence level, and even further down to 1 ppb at a lower confidence level. Lower confidence level is attributed to electronic noise, interfering chemicals, and pressure fluctuation in the gas.

Depending on the choice of catalyst, operating voltage, and concentration of the electrolyte solution, the sensor will respond to specific species with little to no interference from other molecules. When more than one species capable of oxidation at the anode is present, selectivity for the target organic molecule is achieved by control of the threshold voltage at which point reaction takes place or by proper use of sorbents such as activated carbon, molecular sieves, or silver-coated alumina, silica, or other zeolites.

For example, a gas sample may contain both ethylene and 1-methylcyclopropene, both of which are capable of being oxidized at the anode. A lower voltage is needed to oxidize the 1-methylcyclopropene, so, if the detection of 1-methylcyclopropene is of interest, the anode voltage can be set such that the 1-methylcyclopropene is oxidized, but not the ethylene. If ethylene detection is important in such a case, two sensors can be used in parallel, one operating at a slightly lower voltage for detection of 1-methylcyclopropene where no ethylene reaction takes place, and the other operating at a higher voltage at which both 1-methylcyclopropene and ethylene are oxidized. By using the information from both of these sensors, the concentration of 1-methylcyclopropene and ethylene can be simultaneously determined. This protocol can be adapted for use with other pairs (or higher numbers) of oxidizable species.

Many other potentially interfering compounds may be removed by running the gas stream through a sorbent tube, such as activated carbon, molecular sieve, and silica gel likely to adsorb many of the species that could interfere with the signal except for the target organic molecule itself Ethylene, for example, does not adsorb in these sorbents as readily as $C_3$ and larger molecules at room temperature.

When a gas stream containing the target molecule is passed through the sensor, the sensor responds almost instantaneously to changing freestream concentrations. The overall system response time is often less than 10 seconds, with that of the electrolytic cell itself often being 1 second or less, particularly when operated in a pulsed exposure mode. Further, if the concentration in a steady field is to be measured, one is able to operate the system in such a way that the sensitivity of the device will significantly increase. By allowing the anode to come to a full equilibrium with the environment during the time that no voltage is provided to the anode, then by pulsing the voltage provided to the anode during operation, extremely high currents can be realized for a short time. The amplitude of this signal is related to the steady-state concentration in the gas sample flowing over the sensor.

During operation, the sensor of the invention often will pass a small amount of leakage current, even if no target gas is being presented to the anode. To further improve accuracy, this leakage current is preferably subtracted from the measured current signal to give more accurate results. The leakage current may tend to drift over time, and thus it is preferred to periodically re-measure the leakage current during operation. To do this, the anode should not be in contact with the target organic molecule during the time the leakage current is measured. To this end, the sensor may include means for introducing a reference gas, which does not contain the target organic molecule, to the surface of the anode so that leakage current can be determined. For example, a supply of reference gas can be maintained, and periodically flowed through the sensor (in place of the sample gas). Alternatively, the sample gas can be periodically routed through a scrubber or sorbent prior to being introduced into the sensor. The scrubber or sorbent removes the target organic molecule and thus produces a suitable reference gas.

The sensor of the invention can be made into a small, lightweight unit with small energy requirements. It is useful in a wide range of applications where nearly instantaneous detection of contaminants in a gas stream is needed. An application of particular interest is detection and monitoring of ethylene in FF&V and/or fresh flower storage or transportation facilities, where ethylene gas can both act as a ripeness indicator as well as a ripening agent. This technology is simple and is designed to be extremely cost-effective such that users within the agricultural market would be able to afford wide spread use of the sensor, both in the field as well as in cold storage facilities.

The sensor of the invention can be used as a control mechanism for the operation of a scrubbing system that removes one or more target organic molecules from a gas (or portion thereof). In such cases, the scrubbing device operates in response to the generation of an electrical signal which is produced by the sensor, indicating the presence of the target organic molecule in the gas (or sampled portion thereof) at some threshold level or above.

The threshold level may be simply the lower limit of detection of the sensor. Alternatively, the threshold level may be some predetermined level which is above the lower limit of detection of the sensor. For example, the threshold level may be indicated by some specific minimum amount of current that is produced by the sensor in response to the presence of the target organic molecule in the sampled portion of the gas.

When the sensor produces a current in response to the presence of the target organic molecule, the gas (or some portion thereof) is scrubbed to remove the target organic molecule. If desired, the gas can be sampled continuously or intermittently as the scrubbing operation proceeds, using the sensor of the invention, to monitor the removal of the target organic molecule. When the concentration of the target organic molecule is reduced to some predetermined level (such as below the threshold level described before), the electrical current produced by the sensor of the invention will cease or be reduced to below some predetermined level, and the scrubbing step can be discontinued in response thereto.

The nature of the scrubbing operation is not especially important, provided that the scrubbing step can be operated in response to the electrical current produced by the sensor of the invention. As mentioned before, scrubbing can be performed using a second cell of the invention (or many such cells), which are operated at higher applied voltages such that the target organic molecule is destroyed by the cell. Alternatively, various types of sorption methods can be used to remove the target organic molecule from the gas. A third approach is to contact the gas with a reagent that reacts with the target organic molecule to convert it to another species, (1) which is more easily removed from the gas (such as a liquid or solid that simply precipitates, for example), and/or (2) the presence of which is acceptable in the gas. For alkenes, especially ethylene, a reagent of choice is ozone.

Thus, in certain embodiments of the invention, the sensor of the invention produces an electrical current which qualitatively or quantitatively indicates the presence of one or more target organic molecules in the gas. Upon creation of such a current, a reagent as just described is contacted with the gas (or some portion thereof) under conditions such that the reagent reacts with the target organic molecule to convert the target organic molecule to another species. The newly-formed species may be removed from the gas or left in it as desired or necessary for the particular system.

In especially preferred systems, the electrical current produced by the sensor of the invention quantitatively indicates the concentration of the target organic molecule in the gas. In such a case, the electrical current can be used directly or indirectly to control the amount of reagent that is contacted with the gas (or portion) thereof to remove the target organic molecule. In cases in which the volume of gas to be treated is fixed, the electrical signal that indicates the concentration of the target organic molecule is also indicative of the total amount of the target organic molecule in the volume of gas. In such cases, the amount of reagent that is needed to react with all of the target organic molecules in the gas is also known, and that amount of reagent (or some predetermined excess, if desired) can be contacted with the gas to remove the target organic molecule.

Similarly, if the volume of gas to be treated is not fixed, the amount of target organic molecules contained in a given volume of the gas is nonetheless indicated by the electrical current (when the electrical current provides a quantitative indication of the target organic molecule concentration), and the scrubber can be operated in an analogous manner, by contacting known volumes of gas with an amount of reagent (or some excess, if desired) that is needed to react with all of the target organic molecules in the known volume of gas.

In an analogous way, the gas containing the target organic molecule can be treated at known volumes/unit time (such as by passing the gas through the scrubber at known flow rates). The amount of reagent that is needed to treat the gas (or to provide some predetermined excess of reagent) is readily determined from the quantitative information provided by the electrical current created by the sensor of the invention, together with the known volume or flow rate of the gas. Accordingly, the reagent can be provided to (or produced by) the scrubber at a corresponding rate, such that the rate at which the reagent is provided (or produced) is at some predetermined ratio to the rate at which the gas (or target organic molecule) is fed to the scrubber. In such embodiments, flow rate of the gas through the scrubber and the ratio of reagent to target organic molecule can be regarded as fixed, in which case the electrical signal produced by the sensor is qualitatively indicative of the amount of reagent that is needed per unit time. Alternatively, the flow rate of the gas can be monitored, and, through use of computing means, the rate at which the reagent is provided or produced by the scrubber can be varied in real time in response to the concentration of target organic molecule in the gas and the flow rates of gas through the scrubber.

In the preceding embodiments, a highly preferred reagent is ozone. When ozone is the reagent, it is often desirable that little or no excess of ozone be present in the system, because ozone is highly reactive and may engage in a number of undesirable reactions in addition to the desired one with the target organic molecule. An example of this is in fruit and vegetable storage or transportation systems, in which exposing fruit or vegetables to ozone can damage them.

Figure 7:
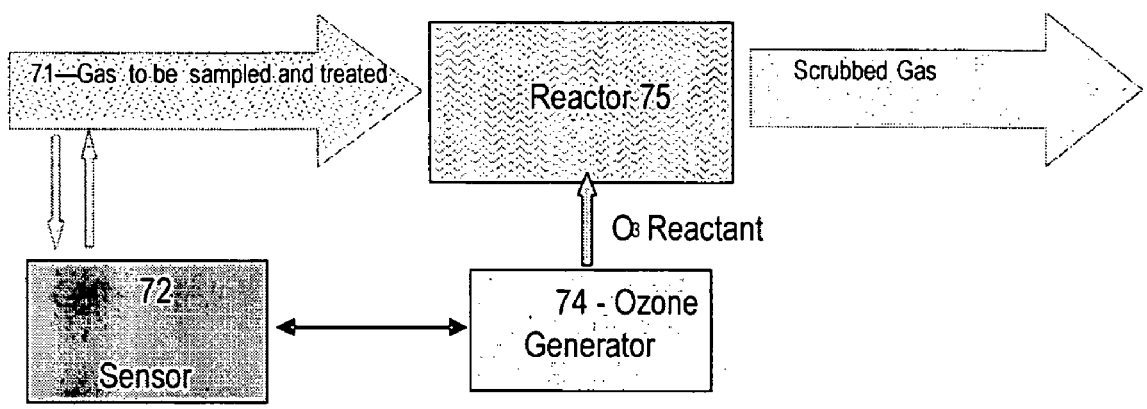
FIG. 7 is schematic diagram illustrating an embodiment of a process of the invention.

FIG. 7 illustrates one type of scrubbing system of the invention, which is useful in fresh fruit, vegetable and or fresh flower storage applications (as well as others). Reference number 71 indicates a volume of gas which is to be sampled and, if necessary, treated to remove a target organic molecule such as ethylene or 1-methylcyclopropene. A sample of the gas is directed into sensor 72 (of the invention) and returned to the main volume of gas. The presence (and in preferred embodiments, the concentration) of the target organic molecule in the sampled portion of the gas produces a current, which can be used directly or indirectly as a control signal, through which ozone generator 74 is operated. When the target organic molecule is present in the sampled gas (as indicate by the production of an electrical current by the sensor), ozone is generated in ozone generator 74, and provided into reaction zone 75. The gas or a portion thereof is also fed into reactor 75, in which the target organic molecule reacts with the ozone and is converted to another species. The new species may be removed from the gas (such as by sorption, precipitation, filtration or other means) or may be left in the gas if desired. Treated gas (represented by arrow 76) is then returned.

The system illustrated in FIG. 7 may be operated such that the amount of ozone provided to reactor 75 by ozone generator 74 is in some predetermined relation to the concentration of target organic molecule in the gas. As described before, this can be done when the electrical current generated by sensor 72 is indicative of the concentration of the target organic molecule in the gas, and either the volume of gas or its flow rate through reactor 75 are known.

The scrubbing system diagrammed in FIG. 7 may be incorporated into other air conditioning systems, such as heating and/or cooling systems, humidification/dehumidification air filtration systems, and the like. In particular, reactor 75 can contain heating and/or cooling elements and/or various types of filters, so that scrubbing is performed simultaneously with other air conditioning operations. Alternatively, those other air conditioning operations can be performed sequentially to the scrubbing operation, by including the necessary apparatus upstream and/or downstream of reactor 75.

In FIG. 7, reactor 75 may contain a packing that adsorbs the target organic molecule from the gas. The packing may be, for example, an inert material such as silica that has a metal coating. The metal is one as described before that adsorbs the target organic molecule. For alkene absorption, gold, silver, platinum and copper are suitable metals. In such an embodiment, after the target organic molecule is adsorbed, the gas is discharged from reactor 75. Ozone is provided to reactor 75 from ozone generator 74, as before. The ozone reacts with the adsorbed target organic molecule at the surface of the packing within reactor 75 to convert the target organic molecule to another species. As before, the control signal produced by sensor 72 may quantitatively or qualitatively indicate the presence of the target organic molecule in gas 71. If the control signal provides a qualitative indication, it can be used to control the amount of ozone produced by ozone generator 74, in the same manner as described before.

The following example is provided to illustrate the invention but is not intended to limit the scope thereof.

Example 1

A 7-mil Nafion membrane (from Ion-Power, Bear, Del.) is immersed in cold nitric acid in a one liter tall-form beaker. The acid is heated to boiling and maintained in that state for one hour. The membrane is then removed form the acid bath and rinsed several times with distilled water. The membrane is then immersed in distilled water and boiled for an additional hour. Treated membrane samples are then stored in distilled water until needed for plating.

Samples of the Nafion film are cut into 7.0 by 10.0 cm rectangles. The rectangles are clamped into a plating fixture which leaves two 3.6 by 7 cm sections of each side of the film exposed. The plating fixture is then inserted vertically into a Teflon plating cell, the fixture forming a barrier between a gold chloride solution on one side of the fixture and a sodium borohydride reducing solution on the other side of the fixture. A series of gold-plated Nafion films are prepared by contacting the films with using various gold chloride and sodium borohydride solutions, and varying plating times.

Film sample no. 1 is prepared using a solution of 0.01 M $HAuCl_4$ in 0.5M HCl. This is prepared by adding $AuCl_3$ or $Au(OH)_3$ into a hydrochloric acid solution. The reducing solution is 1 M sodium borohydride and 1 M NaOH in water. Plating continues for 5 hours. The electrical resistance of the plated film is evaluated at distances of 1 cm across the surface, and found to be $10^5$ ohms.

Film sample no. 2 is prepared using a solution of 0.01 M $HAuCl_4$ in 1.25 M HCl and a reducing solution of 1 M sodium borohydride and 1 M NaOH in water. Plating is continued overnight. The electrical resistance of the plated film is evaluated at distances of 1 cm across the surface, and found to be 0.8 ohms.

Film sample no. 3 is prepared using a solution of 0.01 M $HAuCl_4$ in 0.1 M HCl and a reducing solution of 1M sodium borohydride and 1 M NaOH in water. Plating is continued overnight. The electrical resistance of the plated film is evaluated at distances of 1 cm across the surface, and found to be 0.4 ohms.

Film samples no. 4 and 5 are prepared using a solution of 0.01 M $HAuCl_4$ with one drop of 12 M HCl added/100 ml of solution. The reducing solution is 0.2 M sodium borohydride and 1 M NaOH in water. Plating is continued overnight. The electrical resistances of plated film sample no. 4 and film sample no. 5 are found to be 0.3 ohms and 0.9 ohms, respectively.

Film sample no. 6 is made in the same manner as film samples no. 4 and 5, except the plating solutions are stirred during the plating operation, and plating time is reduced to 1 hour. The resistance of the plated film is 0.4 ohms.

All of the film samples are allowed to dry and are observed visually. Film sample no. 1 has a shiny gold base that appears to be just under the surface of the Nafion film. Film sample nos. 2-6 have somewhat rougher-looking gold surfaces. Photomicrographs of film sample no. 2 shows that the deposited gold has a rough surface structure with noticeable pores. Some cracks appear in the gold plate, which are believed to be due to shrinkage of the plated film as it is dried after the plating process.

Plated film sample no. 2 is mounted into an electrolytic cell as described in FIG. 2. Working electrode 26 is made from a 99.99% gold foil 0.78 mm thick. Counter electrode 27 is a 99.99% gold wire 1.25 mm in diameter. Reference electrode 28 is a mercury/mercurous sulfate electrode. The volume of the electrolyte solution (0.5 M $H_2SO_4$) in cavity 22 is 50 mL. Rear housing 21 is fabricated from a polycarbonate resin.

A model 273-A potentiostat/galvanostat (Princeton Applied Research, Oak Ridge, Tenn.) operated with CorrWare software (Scribner Associates, Southern Pines, N.C.) is used to evaluate the electrochemical properties of the electrolytic cell. With software control, the Model 273-A potentiostat/galvanostat provides a current that ranges from 1 μA to 1 A. The accuracy of this instrument in the current ranges most applicable to the ethylene sensing device, which are less than 10 μA, is better than 0.5% of range. The input impedance is approximately $10^{10}$ Ω.

Fresh 0.5 M $H_2SO_4$ is added to the electrolyte chamber of the test cell at the end of each day's testing, the electrolyte is replaced with fresh solution and again each morning prior to testing.

Test gas samples are supplied to the sensor through a tube connected to inlet 29 at a rate of 100 sccm.

Cyclic voltammetry measurements are made, where cell currents are obtained as a function of applied potential (from 0 to 1.2 volts relative to the reference electrode) under polarization of the working electrode. Such measurements allow potentials to be established where ethylene is oxidized to acetaldehyde, but below the onset of oxidation of the gold electrode. The area from 0 to 0.7 volts relative to the reference electrode is shown to be free from competing reactions, when a nitrogen/ethylene test gas is used. These measurements establish that an applied voltage of about 0.52 volts relative to the reference electrode (1.16 volts relative to SHE) is sufficient to oxidize ethylene without oxidizing the gold anode.

Figure 5:
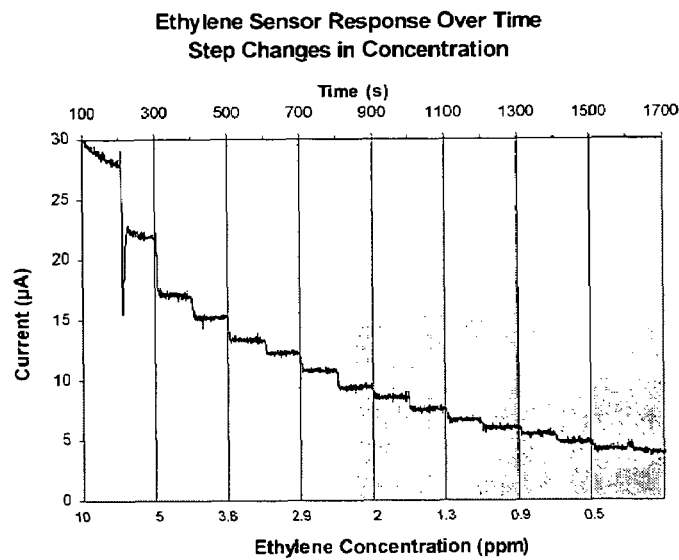
FIG. 5 is a graphical representation of current produced by an embodiment of the sensor of the invention with respect to varying ethylene concentrations in a sample gas.

A voltage of 0.52 volts (relative to the reference electrode) is then applied to the anode, and a stream containing 10 ppm of ethylene in nitrogen is fed to the sensor. The current produced from the oxidation of the ethylene at the anode is measured. The concentration of ethylene in the gas is reduced stepwise to about 500 ppb by blending the sample gas with additional nitrogen. The current produced at the anode is measured each time. Results are indicated graphically in FIG. 5. The data illustrated in FIG. 4 shows that current produced is closely proportional to the ethylene concentration in the sample gas, which permits quantitative detection of ethylene within this range of concentrations. About a 10 second period is required for the sensor to respond to changes in ethylene concentration. The response time is attributed to both flow time in the connecting tubing and the kinetics of adsorption of ethylene into the gold electrode.

Figure 6:
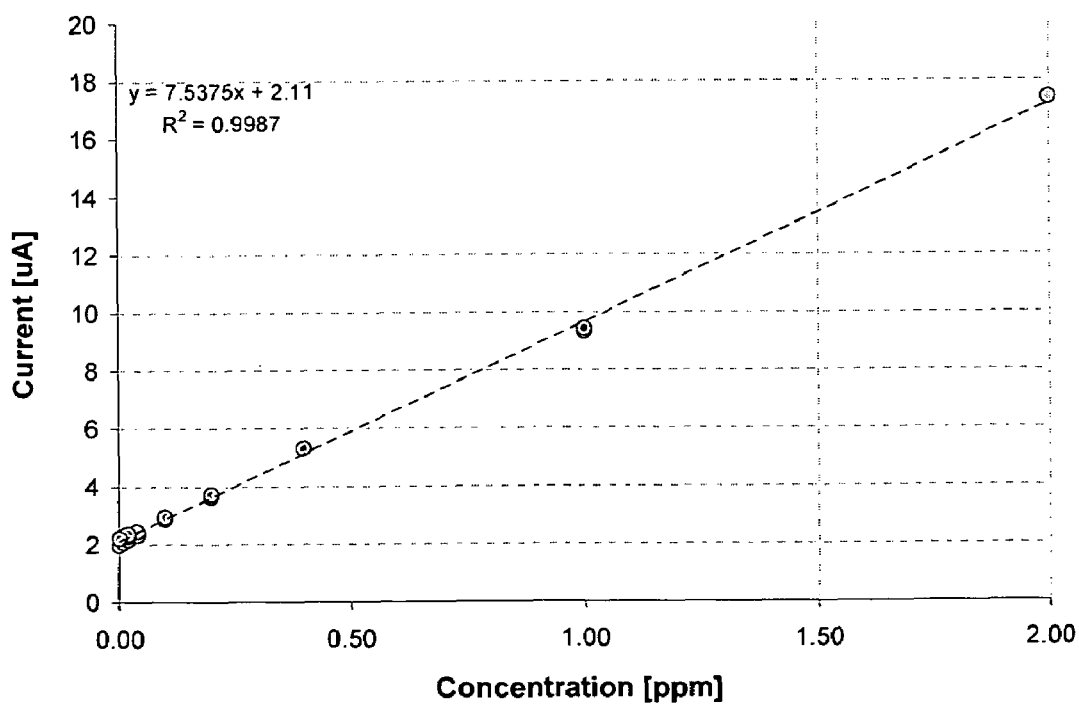
FIG. 6 is a graphical representation of current produced by an embodiment of the sensor of the invention with respect to varying ethylene concentrations in a sample gas.

Further testing is done in the same manner, using ethylene concentrations from 0 to 2000 ppb in nitrogen. The current produced is plotted against ethylene concentration in FIG. 6. The plot in this figure shows extremely linear response with respect to ethylene concentrations all the way down to 10 ppb.

Example 2

Film sample no. 6 from Example 1 is mounted as the anode in an electrochemical cell as shown in FIGS. 2 and 2A. Housing 220 and cap 240 are constructed of a molded polycarbonate resin. The film is supported by ribs to prevent it from flexing during the test. The counter electrode and reference electrode are each graphite rods. The electrolyte solution contained in cavity 222 is 0.05 M $H_2SO_4$.

A Custom Sensor Solutions model 1401 potentiostat is used to evaluate the electrochemical properties of the electrolytic cell. The potentiostat provides a known voltage across the cell from anode 224 to counter electrode 227.

The apparatus is tested by introducing a sample gas that is pulsed with ethylene. A nitrogen flow is supplied to the sensor, from a pressurized source, and through a tube connected to inlet 231 at a flow rate of 200 sccm. Varying concentrations of nitrogen are intermittently introduced into the nitrogen flow. The sensor produces a current of approximately 4 microamps per part per million ethylene in the sample. The response is essentially linear with ethylene concentration from about 10 parts per billion to about 10 parts per million.

Further tests are conducted using the same apparatus, but varying the electrolyte pH from about 0.5 to about 6, and an ethylene concentration in the sample gas of 10 ppm. The sensitivity of the sensor is found to decrease as the pH of the electrolyte increases over this range.

Further tests are conducted, again using the same apparatus and a 10-ppm ethylene concentration in nitrogen, at varying temperatures from 10 to 45° C. Over this temperature range, sensitivity increases from about 3.3 to about 6 microamps/ppm ethylene. These results indicate that the sensor is operable over this entire range, and thus is suitable for use in refrigerated conditions as well as warm environments. Further, these results indicate that in preferred embodiments, currents produced by the sensor should be normalized to temperature, particularly when the device is used to provide quantitative measurements of the target organic molecule concentration.

In another experiment, a single apple is placed in a closed 0.5 liter jar at room temperature, where they release ethylene. The atmosphere in the jar is recirculated through the sensor to measure the ethylene concentration. The ethylene concentration from the single apples is measured at about 1 ppm within 3 minutes of the time the apple is place in the jar. The ethylene concentration increases to approximately 7 ppm after about 20 minutes. The ethylene concentration in the atmosphere in the jar is also measured by gas chromatography, which provides very similar results.

The invention claimed is:

1. A sensor comprising a) an electrolytic cell having an anode that adsorbs ethylene, b) means for measuring current created by an electrocatalytic reaction of ethylene at the anode, c) and intake means for supplying a sample gas to the anode, wherein the electrolytic cell includes (1) a front housing that includes a gas inlet and a gas outlet, (2) a rear housing that includes a cavity for containing said electrolyte; and (3) an anode positioned between said front and rear housings, wherein said anode is supported to minimize or eliminate flexing and is exposed on one side to the electrolyte contained in the cavity in said rear housing and on the other side to a sample gas in the front housing, and further wherein the front housing includes a microchannel geometry or surface features which produce turbulent flow characterized by a Reynolds number of at least 500 in a sample gas flowing through said front housing at a flow rate of from 5 to 3000 sccm and still further wherein the front housing functions as a working electrode and the rear housing contains multiple support pegs which provide mechanical support and current collection capability to the anode, wherein the electrolytic cell detects the presence of ethylene in a gas stream at levels as low as 10 parts per billion.

2. The sensor of claim 1, wherein said rear housing includes inlet and outlet ports for filling, emptying and recirculation of an electrolyte.

3. The sensor of claim 1 wherein the anode includes a solid-semi-permeable membrane that is coated or plated with gold.

* * * * *